(12) United States Patent
Pu

(10) Patent No.: US 7,947,969 B2
(45) Date of Patent: May 24, 2011

(54) STACKED CONFORMATION RADIOTHERAPY SYSTEM AND PARTICLE BEAM THERAPY APPARATUS EMPLOYING THE SAME

(75) Inventor: Yuehu Pu, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 488 days.

(21) Appl. No.: 12/023,134

(22) Filed: Jan. 31, 2008

(65) Prior Publication Data

US 2009/0003524 A1     Jan. 1, 2009

(30) Foreign Application Priority Data

Jun. 27, 2007   (JP) .................................. 2007-168535
Jan. 8, 2008    (JP) .................................. 2008-001401

(51) Int. Cl.
*A61N 5/10*     (2006.01)

(52) U.S. Cl. ............... 250/505.1; 250/492.1; 250/492.3; 250/396 ML; 250/493.1; 378/65; 378/147; 378/152; 313/359.1; 315/502; 315/503; 315/505

(58) Field of Classification Search .............. 250/492.1, 250/492.3, 396 R, 396 ML, 493.1, 505.1, 250/515.1, 503.1; 378/65, 147, 152; 313/359.1; 315/502, 503, 505
See application file for complete search history.

(56) References Cited

U.S. PATENT DOCUMENTS

| | | | | |
|---|---|---|---|---|
| 5,012,111 A * | 4/1991 | Ueda | ........................ | 250/492.3 |
| 5,017,789 A | 5/1991 | Young et al. | | |
| 6,265,837 B1 * | 7/2001 | Akiyama et al. | ............... | 315/503 |
| 6,984,835 B2 * | 1/2006 | Harada | ....................... | 250/505.1 |
| 7,054,801 B2 * | 5/2006 | Sakamoto et al. | .............. | 703/13 |
| 7,629,598 B2 * | 12/2009 | Harada | ....................... | 250/492.3 |
| 2002/0128807 A1 | 9/2002 | Sakamoto et al. | | |
| 2005/0099145 A1 * | 5/2005 | Nishiuchi et al. | ............. | 315/500 |
| 2005/0231138 A1 * | 10/2005 | Nakanishi et al. | ............ | 315/500 |
| 2006/0231775 A1 * | 10/2006 | Harada | ....................... | 250/492.3 |

FOREIGN PATENT DOCUMENTS

| | | |
|---|---|---|
| JP | 2000-331799 (A) | 11/2000 |
| JP | 2001-326098 (A) | 11/2001 |
| JP | 2005-103255 (A) | 4/2005 |
| JP | 2006-288875 (A) | 10/2006 |

OTHER PUBLICATIONS

Komori et al., "Optimization of Spiral-Wobbler System for Heavy-Ion Radiotherapy", Japanese Journal of Applied Physics vol. 43, No. 9A, 2004, pp. 6463-6467.*  German Office Action dated Jul. 28, 2010 in a corresponding patent application and an English-language translation thereto, 12 pages.
Kanai, T et al, "Biophysical Characteristics of Himac Clinical Irradiation System for Heavy-Ion Radiation Therapy," I.J. Radiation Oncology•Biology•Physics•, vol. 44, No. 1, 1999, pp. 201-210.

* cited by examiner

*Primary Examiner* — Bernard E Souw
*Assistant Examiner* — Michael J Logie
(74) *Attorney, Agent, or Firm* — Buchanan Ingersoll & Rooney PC

(57) ABSTRACT

A stacked conformation radiotherapy system capable of homogenizing a radiation dose distribution, including an irradiation head and irradiation control means. The irradiation head projects a particle beam accelerated by an accelerator, toward an object to-be-irradiated, and it includes wobbler electromagnets for deflecting and scanning the particle beam. In carrying out stacked conformation radiotherapy by deflecting and scanning the particle beam, the irradiation control means subjects the wobbler electromagnets to magnetization controls so that the particle beam may depict a one-stroke revolving orbit which begins with a start point and returns to the start point, and it performs a control so that the irradiation period of the particle beam to be outputted from the irradiation head may become integral times a wobbler cycle which is required for the particle beam to make one revolution of the revolving orbit.

6 Claims, 13 Drawing Sheets

[FIG. 1]
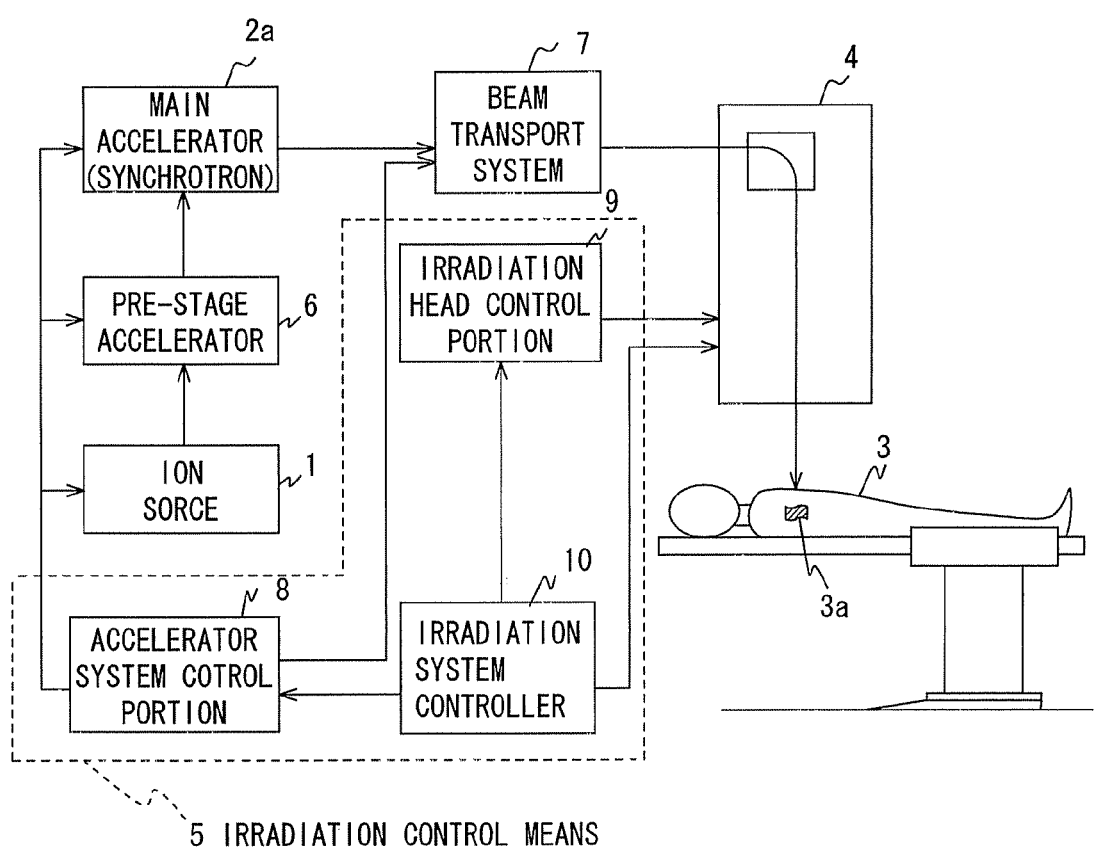

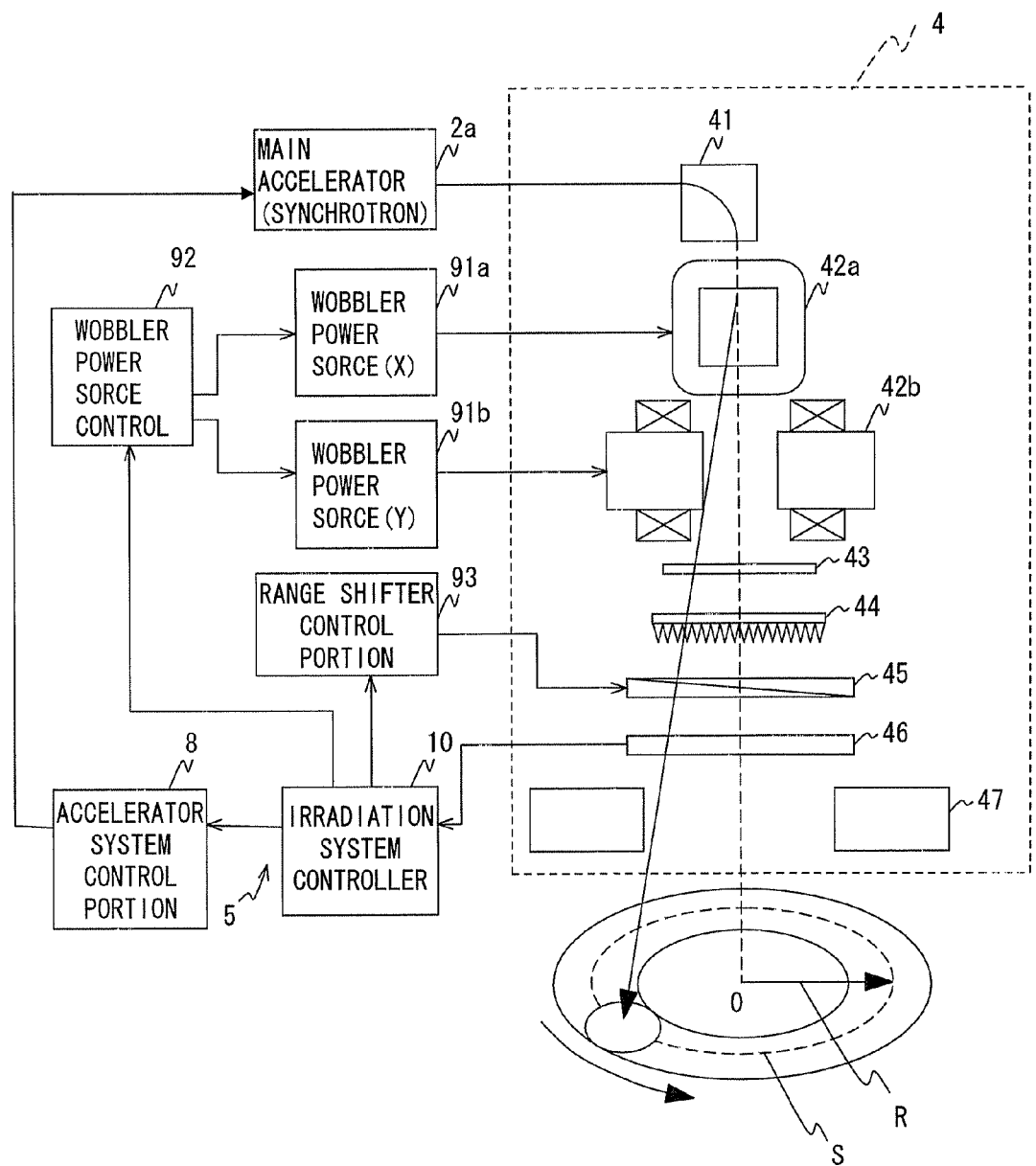
[FIG. 2]

[FIG. 3]
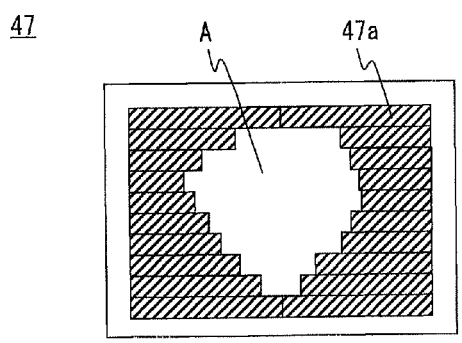
[FIG. 4]
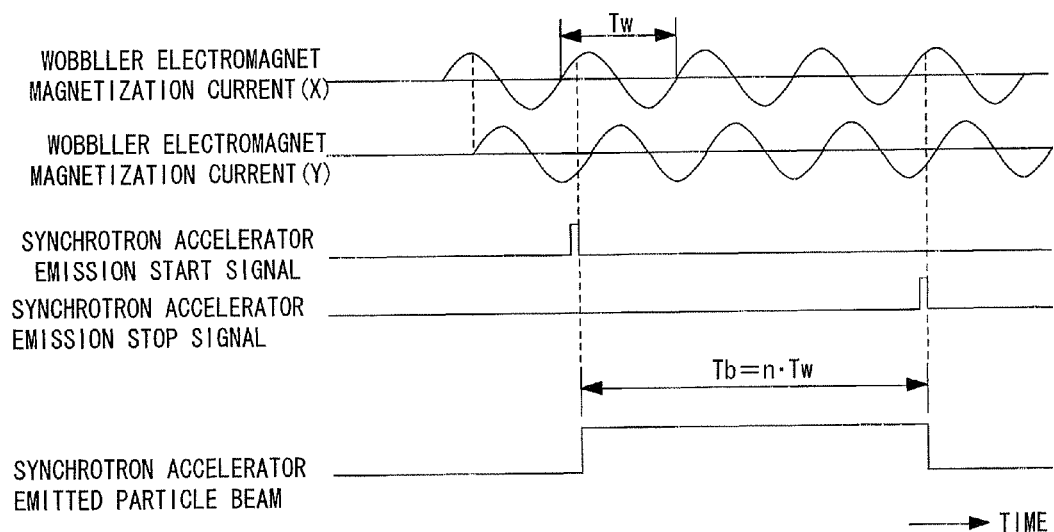

[FIG.5]
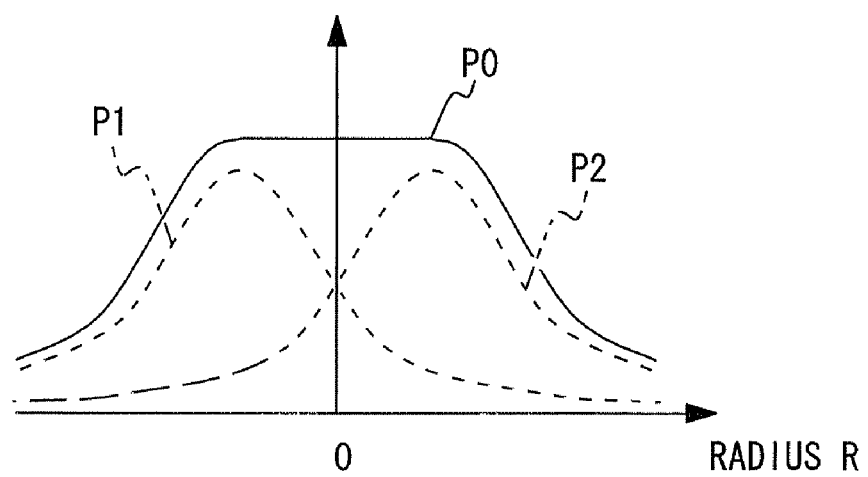

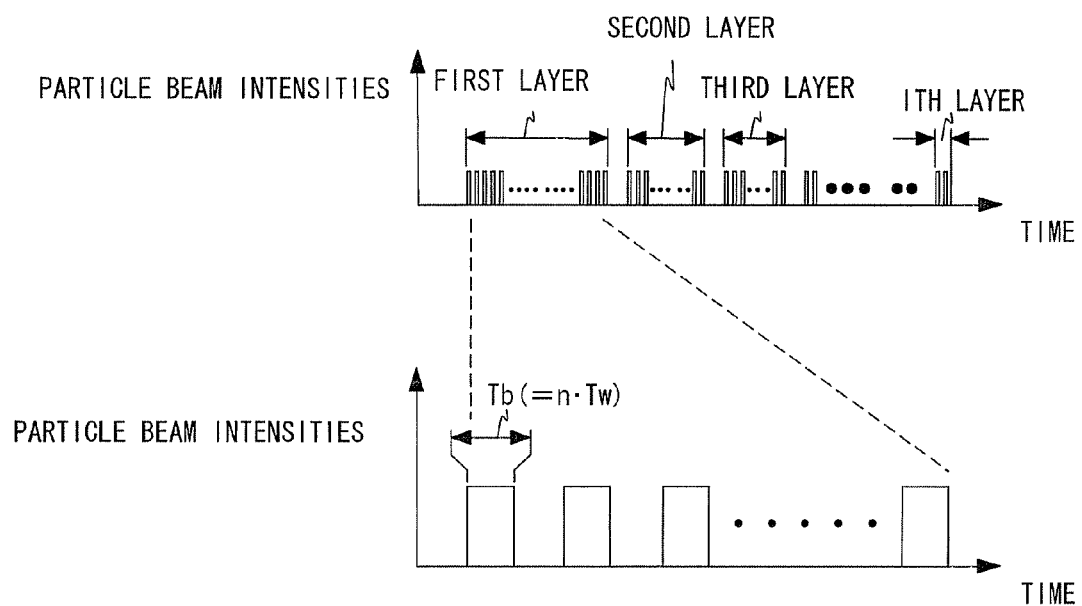
[FIG. 6]
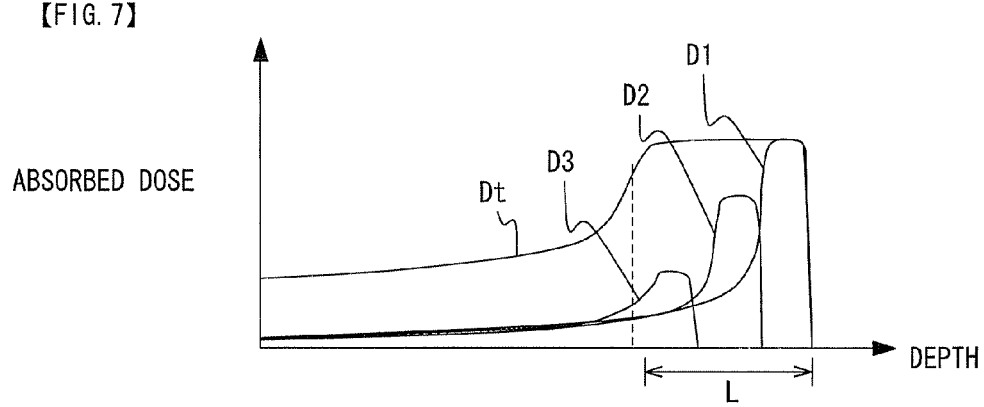
[FIG. 7]

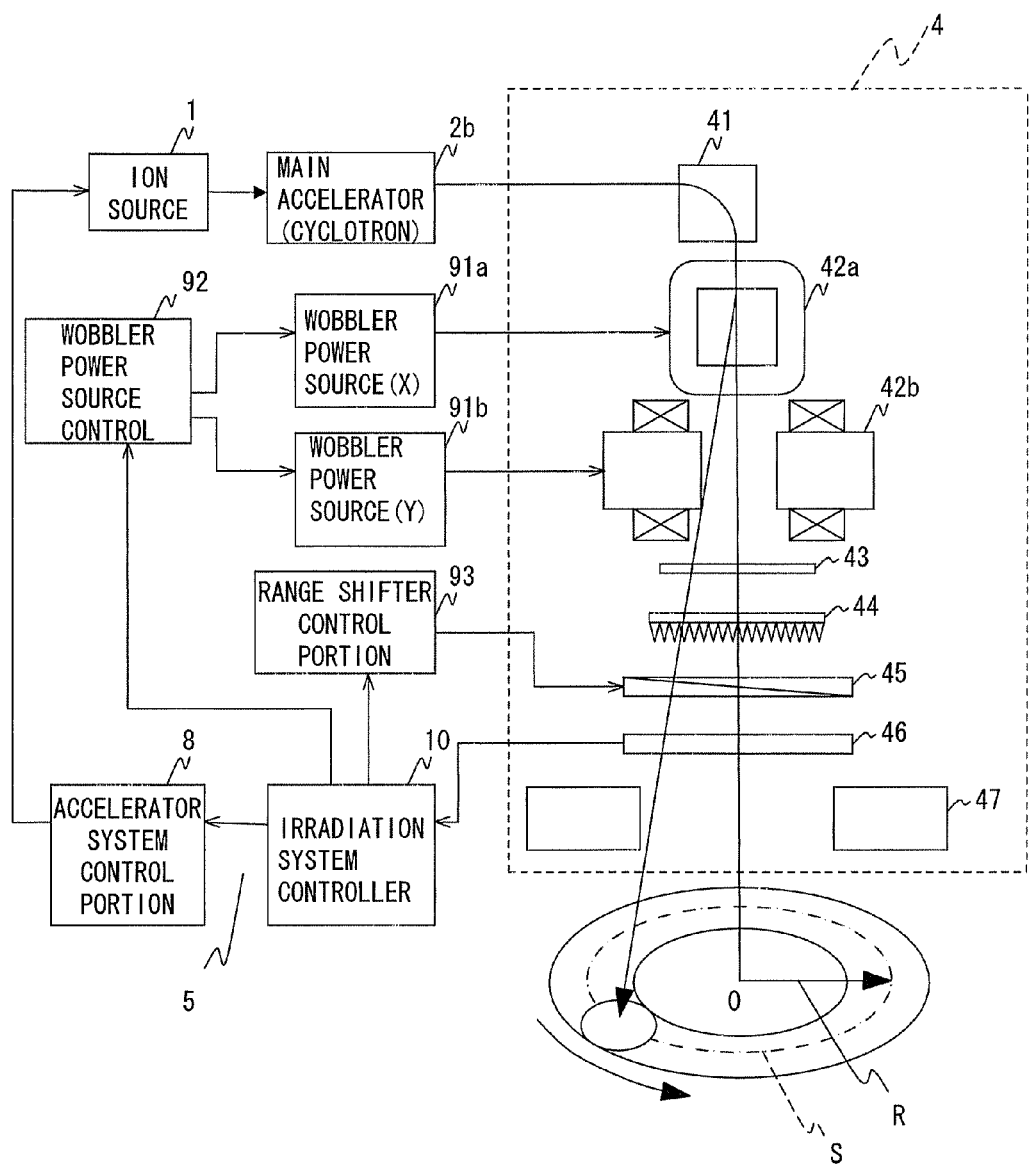
[FIG. 8]

[FIG. 9]
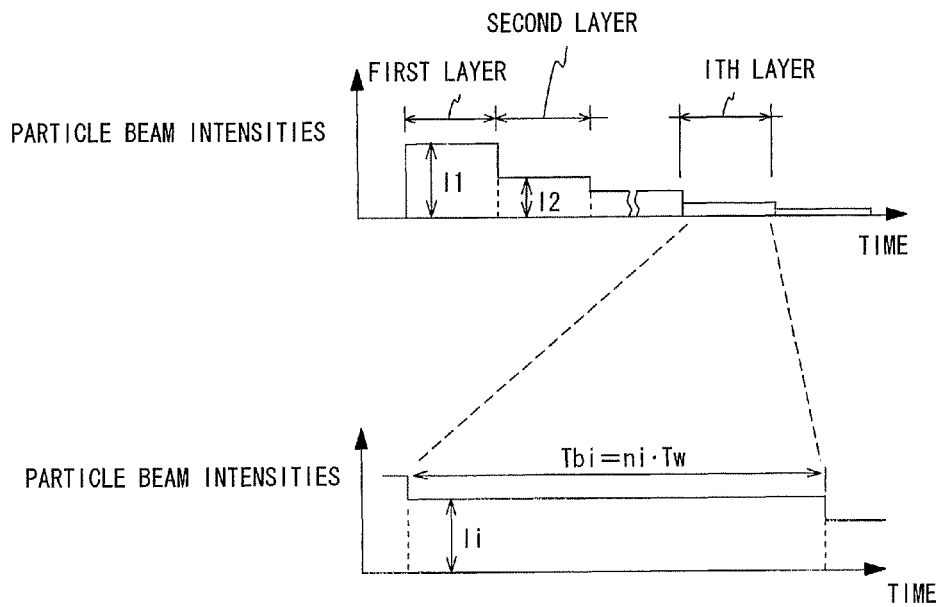
[FIG. 10]
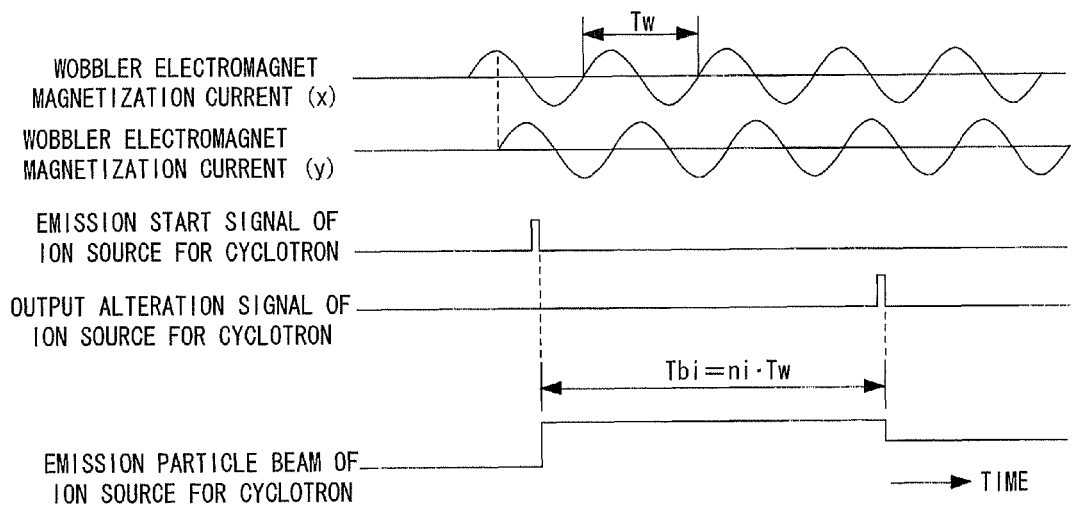

[FIG. 11]
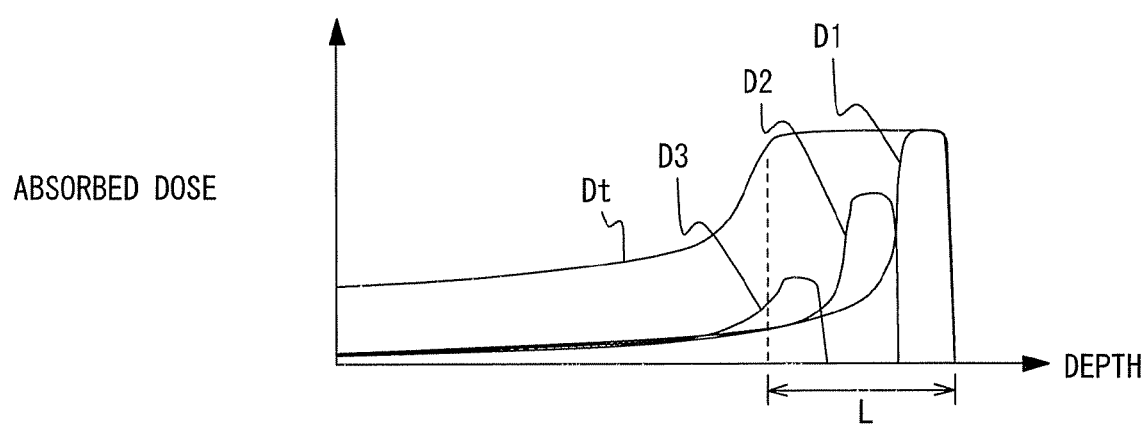

[FIG. 12]
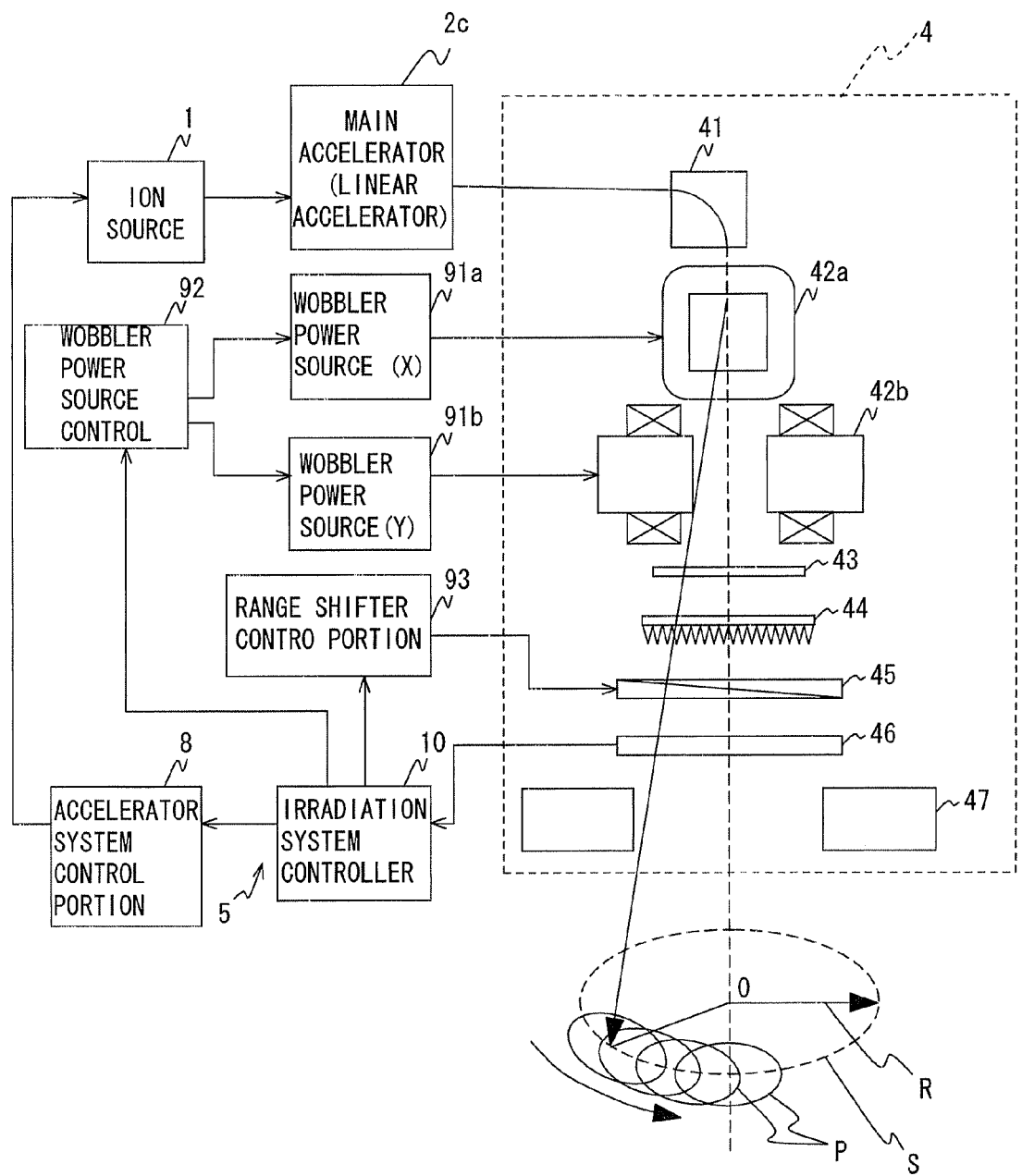

[FIG. 13]
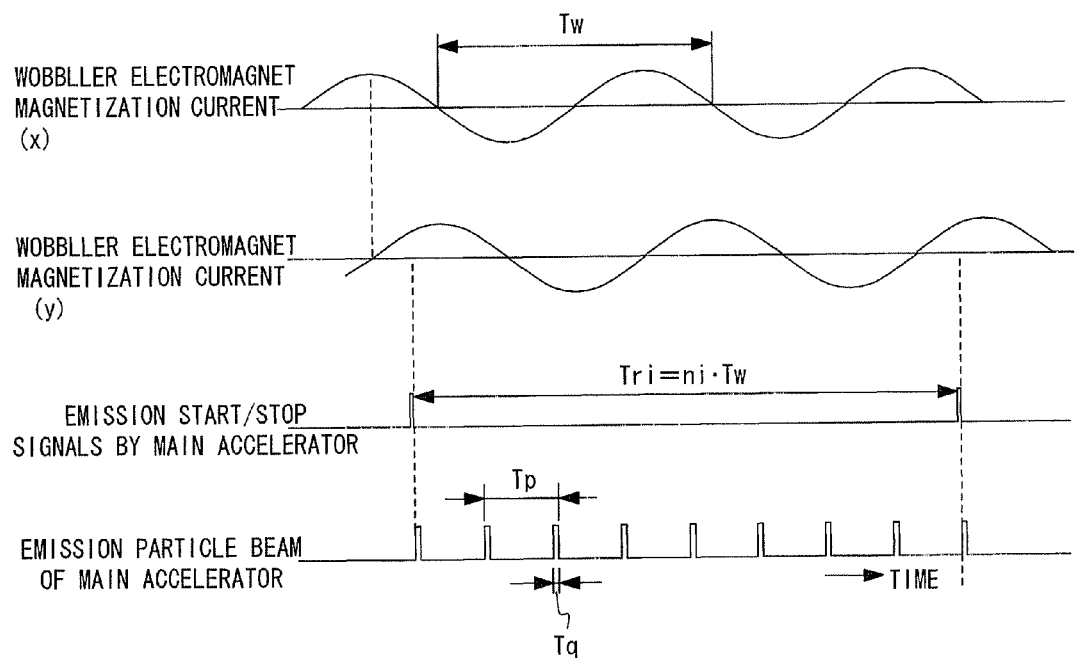
[FIG. 14]
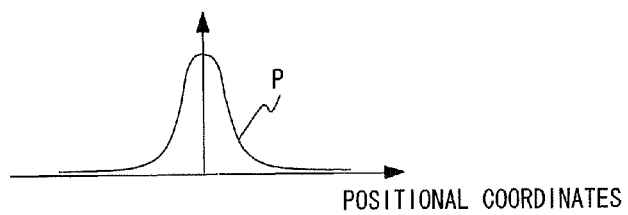

[FIG. 15]
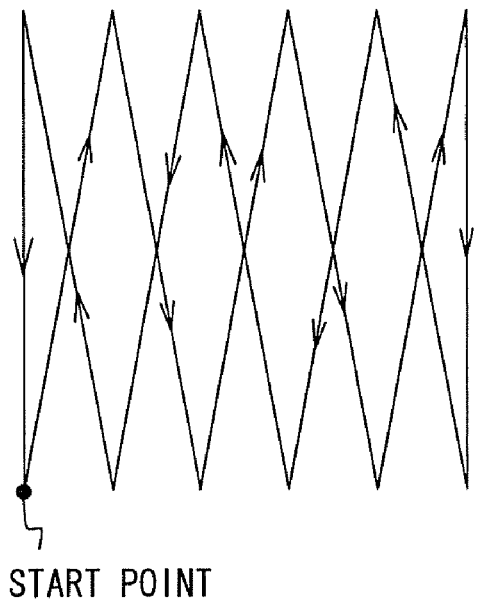
START POINT
[FIG. 16]
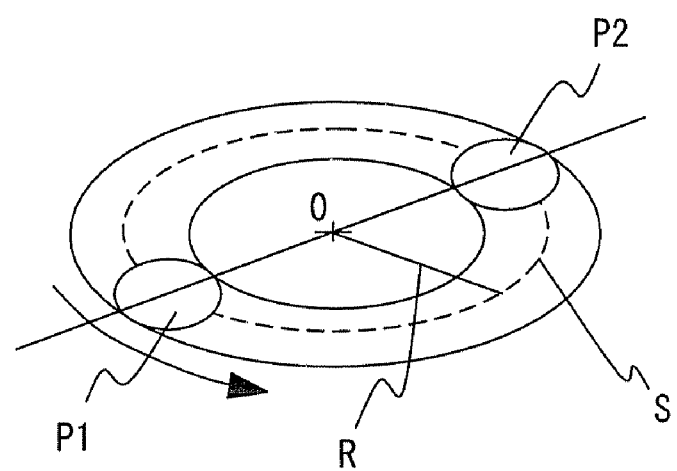

[FIG.17]
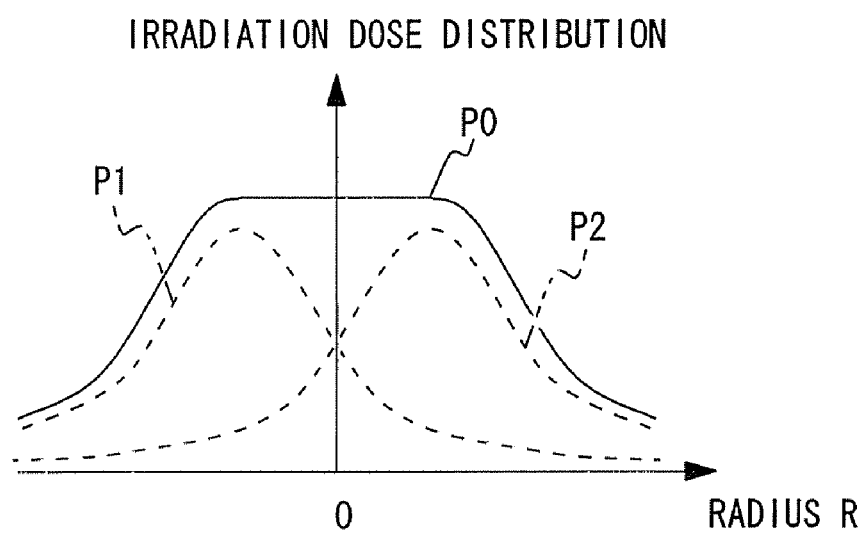

[FIG. 18]
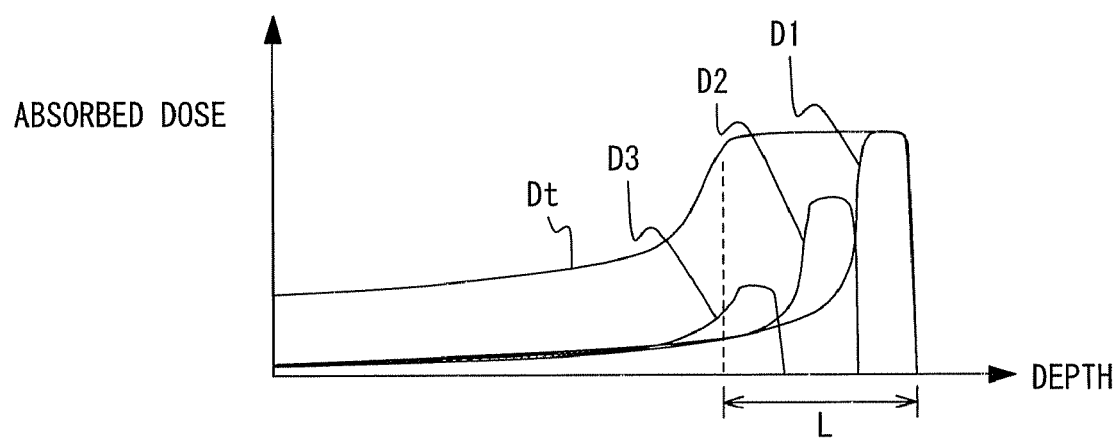

STACKED CONFORMATION RADIOTHERAPY SYSTEM AND PARTICLE BEAM THERAPY APPARATUS EMPLOYING THE SAME

BACKGROUND OF THE INVENTION

1. Field of the Invention

The present invention relates to a stacked conformation radiotherapy system which irradiates a diseased part with a particle beam of carbon, neon or the like in three dimensions for the purpose of the therapy of a cancer, a malignant tumor or the like, and a particle beam therapy apparatus which employs the stacked conformation radiotherapy system.

2. Description of the Related Art

In order to irradiate a diseased part with a particle beam of appropriate dose for the purpose of the therapy of a cancer, a malignant tumor or the like, a conformability needs to be heightened by performing so-called "stacked conformation radiotherapy" in which the irradiation region of the particle beam is brought into agreement with the shape of the diseased part existing in three dimensions. To this end, it is important that the shape (leaf positions) of a multi-leaf collimator is appropriately set, and that both the spatial distributions of an irradiation dose in a horizontal direction (on the plane of an irradiation field) and an irradiation dose in a vertical direction (a depth direction) are homogenized to the utmost so as to apply a homogeneous dose to the whole diseased part.

Here, as a method for homogenizing the dose distributions of the planar irradiation field which irradiates the diseased part, there is a wobbling method (refer to, for example, Patent Documents 1, 2, 3 and 4 being JP-A-2006-288875, JP-A-2001-326098, JP-A-2000-331799 and JP-A-2005-103255, respectively). In the wobbling method, a pair of wobbler electromagnets are arrayed so that the directions of the magnetic fields thereof may become orthogonal to each other, and currents whose cycles are equal and whose phases differ 90 degrees are caused to flow through the respective wobbler electromagnets, thereby to magnetize the wobbler electromagnets. Thus, the particle beam emitted from an accelerator is turned and deflected in orthogonal directions within a plane perpendicular to its traveling direction by the magnetic fields of the wobbler electromagnets. As a result, as shown in FIG. 16, the particle beam depicts a circular revolving orbit S every fixed cycle Tw (hereinafter, a time period which is expended in depicting the revolving orbit S for one revolution shall be called the "wobbler cycle Tw"). On this occasion, when the scattering angle of scattering ascribable to a scatterer disposed midway of the irradiation path of the particle beam and the radius R of the revolving orbit S are optimally set, two particle beam distributions P1 and P2 opposing to each other on the revolving orbit S overlap as shown in FIG. 17, so that a dose distribution P0 in a radial direction becomes a flat distribution within a plane containing a revolving center O. Accordingly, when the particle beam is projected along on the revolving orbit S so as to depict a complete round for one revolution, the dose distribution on the plane of the irradiation field becomes homogeneous.

On the other hand, in order to homogenize the dose distribution in the vertical direction (depth direction), processing has heretofore been executed as shown in FIG. 18. More specifically, the irradiation energy of the particle beam is altered every layer in the depth direction by a range shifter, in correspondence with the size L of the diseased part in the depth direction. Thus, while extended Bragg peaks D1, D2, . . . are being moved along the depth direction, the irradiation dose is heightened more at the deeper layer position of the diseased part, and it is gradually lowered more as the depth becomes shallower. That is, while the extended Bragg peaks D1, D2, . . . are being moved along the depth direction of the diseased part, the irradiation dose is adjusted in accordance with the hierarchy of the irradiation, whereby the whole dose distribution Dt obtained by cumulating the extended Bragg peaks D1, D2, . . . of the respective layers becomes flat in correspondence with the size L of the diseased part in the depth direction.

In this case, since the irradiation dose of the particle beam is higher at the position of the deeper layer, the irradiation time period of the particle beam is proportionally longer if particle beam intensities at the respective layers are equal. At the deeper layer of the diseased part, therefore, the number of revolutions of the particle beam (hereinafter, termed the "number of wobbler revolutions") becomes larger. In other words, as the hierarchy of the irradiation advances more (the irradiation region becomes shallower), the number of wobbler revolutions per a layer becomes smaller.

Meanwhile, in the prior-art stacked conformation radiotherapy as stated in Patent Documents 1-4, the timings of the emission and stop of the particle beam from the accelerator such as a synchrotron, that is, the irradiation period of the particle beam have/has been independent of the wobbler cycle Tw. More specifically, the magnetization signals of the pair of wobbler electromagnets are endowed with a fixed relationship so as to have the phase difference of 90 degrees from each other, but their wobbler cycle Tw is set independently of that irradiation period Tb of the particle beam which is time-divided in order to obtain a predetermined irradiation dose.

On the other hand, in the stacked conformation radiotherapy, the particle beam irradiation is ended when the irradiation dose set every layer beforehand is reached. On this occasion, in the case where the wobbler cycle Tw is set independently of the irradiation period Tb of the particle beam as stated above, the emission of the particle beam from the accelerator is stopped before the particle beam makes one revolution of the revolving orbit, and an unirradiated region which is not irradiated with the particle beam appears at part of the revolving orbit.

Especially, in the stacked conformation radiotherapy, the number of wobbler revolutions per layer becomes smaller gradually as the hierarchy of the irradiation advances more (the irradiation region becomes shallower), as stated before. Therefore, in the case where the irradiation with the particle beam has been stopped midway of the revolving orbit, a place where parts lacking the particle beam irradiations overlap several layers appears, and the dose distribution in the depth direction becomes drastically inhomogeneous.

SUMMARY OF THE INVENTION

The present invention has been made in order to solve the above problems, and it has for its object to provide a stacked conformation radiotherapy system in which an irradiation lacking region appears only once or the irradiation lacking region is always prevented from appearing at any hierarchical level, irrespective of the timings of the emission and stop of a particle beam from an accelerator in stacked conformation radiotherapy, whereby an irradiation dose distribution can be homogenized still more than in the prior art, and a particle beam therapy apparatus which employs the stacked conformation radiotherapy system.

In order to accomplish the object, in the invention, in a system including an accelerator which accelerates a particle beam generated from an ion source, an irradiation head which projects the particle beam accelerated by the accelerator, toward an object to-be-irradiated, and which includes wobbler electromagnets for deflecting and scanning the particle beam, and irradiation control means for carrying out stacked conformation radiotherapy by controlling the ion source, the accelerator and the irradiation head, the irradiation control means deflecting and scanning the particle beam by subjecting the wobbler electromagnets to magnetization controls, a configuration to be stated below is adopted.

That is, in the invention, the irradiation control means performs the magnetization controls of the wobbler electromagnets so that the particle beam may depict a one-stroke revolving orbit which begins with a start point and returns to the start point, and it performs a control so that an irradiation period of the particle beam to be outputted from the irradiation head may become integral times a wobbler cycle which is required for the particle beam to make one revolution of the revolving orbit.

According to the invention, in carrying out stacked conformation radiotherapy using a continuous beam an accelerator, controls are performed so that a particle beam may depict a one-stroke revolving orbit which begins with a start point and returns to the start point, and that the irradiation period of the particle beam to be outputted from an irradiation head may become integral times a wobbler cycle which is required for the particle beam to make one revolution of the revolving orbit. Therefore, it is reliably avoidable that any irradiation lacking part appears on the last revolving orbit of each layer. In other words, it is possible to realize the stacked conformation radiotherapy which is always free from the irradiation lacking region in each layer and in which a dose distribution is homogenized, irrespective of the timings of the emission start/stop of the particle beam. Furthermore in the case where an emission beam of an accelerator is a shape of pulses, it is possible to obtain the dose distribution free from the irradiation lacking region in the irradiation period of each irradiated pulse beam except for the last revolving orbit of each layer.

Accordingly, when the stacked conformation radiotherapy system is applied to a particle beam therapy apparatus, the irradiation control of the particle beam is simplified, and the possibility of an erroneous irradiation can be relieved, so that particle beam therapy of high precision can be carried out.

The foregoing and other objects, features, aspects and advantages of the present invention will become more apparent from the following detailed description of the invention when taken in conjunction with the accompanying drawings.

BRIEF DESCRIPTION OF THE DRAWINGS

FIG. 1 is a block diagram showing the general configuration of a particle beam therapy apparatus to which a stacked conformation radiotherapy system in Embodiment 1 of the present invention is applied;

FIG. 2 is a block diagram showing the principal portions of an irradiation head for projecting the particle beam of the apparatus toward an object to-be-irradiated and irradiation control means for performing the irradiation control of the particle beam;

FIG. 3 is a plan view of the multi-leaf collimator of the apparatus;

FIG. 4 is a timing chart showing the relationships of wobbler electromagnet magnetization currents, the emission start signal and emission stop signal of the particle beam based on a synchrotron accelerator, and the irradiation period of the emitted particle beam by the synchrotron accelerator, with time, in the apparatus;

FIG. 5 is a characteristic diagram showing irradiation dose distributions in a radial direction in the case where the particle beam is circularly deflected and scanned on a plane by the magnetizations of wobbler electromagnets, in the apparatus;

FIG. 6 is a diagrams showing the irradiation patterns of the particle beam in the case where stacked conformation radiotherapy is performed in the apparatus, and showing the relationships between particle beam intensities (at a first layer to an ith layer) and time;

FIG. 7 is a diagram showing the extended Bragg peaks of the individual layers in the stacked conformation radiotherapy, and an absorbed dose distribution after the irradiations of all the layers, in the apparatus;

FIG. 8 is a block diagram showing the principal portions of an irradiation head for projecting a particle beam toward an object to-be-irradiated and irradiation control means for performing the irradiation control of the particle beam, in a particle beam therapy apparatus in Embodiment 2 of the invention;

FIG. 9 is a diagrams showing the irradiation patterns of the particle beam in the case where stacked conformation radiotherapy is carried out in the apparatus;

FIG. 10 is a timing chart showing the relationship among wobbler electromagnet magnetization currents, the emission start signal/output alteration signal of an ion source for a cyclotron accelerator, and the irradiation period of the emission particle beam of the ion source for the cyclotron accelerator, in the apparatus;

FIG. 11 is a diagram showing the extended Bragg peaks of individual layers in the stacked conformation radiotherapy, and an absorbed dose distribution after the irradiations of all the layers, in the apparatus;

FIG. 12 is a block diagram showing the principal portions of an irradiation head for projecting a particle beam toward an object to-be-irradiated and irradiation control means for performing the irradiation control of the particle beam, in a particle beam therapy apparatus in Embodiment 3 of the invention;

FIG. 13 is a timing chart showing the relationship among wobbler electromagnet magnetization currents, the emission start/stop signals of the particle beam by a main accelerator, and the irradiation period of the emission particle beam pulses of the main accelerator, in the apparatus;

FIG. 14 is a characteristic diagram (relation to positional coordinates) showing the dose distribution of an irradiation region which corresponds to each of the particle beam pulses generated in the apparatus;

FIG. 15 is an explanatory diagram showing a situation in the case where a particle beam is deflected and scanned zig-zag on a plane by the magnetizations of wobbler electromagnets;

FIG. 16 is an explanatory diagram showing a situation in the case where a particle beam is circularly deflected and scanned on a plane by the magnetizations of wobbler electromagnets;

FIG. 17 is a characteristic diagram showing irradiation dose distributions in a radial direction in the case where the particle beam is circularly deflected and scanned on the plane by the magnetizations of the wobbler electromagnets; and FIG. 18 is a diagram showing the extended Bragg peaks of individual layers in stacked conformation radiotherapy, and an absorbed dose distribution after the irradiations of all the layers.

DESCRIPTION OF THE PREFERRED EMBODIMENTS

Embodiment 1

FIG. 1 is a block diagram showing the general configuration of a particle beam therapy apparatus to which a stacked conformation radiotherapy system in Embodiment 1 of the present invention is applied, while FIG. 2 is a block diagram showing the principal portions of an irradiation head for projecting the particle beam of the apparatus toward an object to-be-irradiated and irradiation control means for performing the irradiation control of the particle beam.

The particle beam therapy apparatus in Embodiment 1 is chiefly configured of an ion source 1 which generates a particle beam, a synchrotron accelerator 2a being a main accelerator which accelerates the particle beam generated from the ion source 1, an irradiation head 4 which projects the particle beam accelerated by the synchrotron accelerator 2a, toward a diseased part 3a being the object to-be-irradiated of a patient 3, and irradiation control means 5 for performing the irradiation control of the particle beam.

In addition, a pre-stage accelerator 6 which pre-accelerates the particle beam generated by the ion source 1, before the particle beam is guided into the synchrotron accelerator 2a, is interposed between the ion source 1 and the synchrotron accelerator 2a. Besides, a beam transport system 7 for guiding the particle beam from the synchrotron accelerator 2a to the irradiation head 4 is interposed between the synchrotron accelerator 2a and the irradiation head 4.

The synchrotron accelerator 2a turns ON/OFF a gate leading to the beam transport system 7, under the control of an accelerator system control portion 8 to be explained later, thereby to emit the particle beam with a pulse width (beam spill length) Tb which is longer than a wobbler cycle Tw.

On the other hand, the irradiation head 4 is configured by successively arranging along a particle beam orbit, a deflection electromagnet 41 which deflects the particle beam transported by the beam transport system 7, so as to proceed toward the patient, a pair of wobbler electromagnets 42a and 42b by which the particle beam is deflected and scanned, a scatterer 43 which scatters the particle beam so as to have a predetermined divergence angle, a ridge filter 44 by which the energy width of the particle beam is extended, a range shifter 45 by which the irradiation energy of the particle beam is altered in accordance with the depth position of the diseased part 3a, a dose monitor 46 which monitors the irradiation dose of the particle beam, a multi-leaf collimator 47 by which the irradiation field of the particle beam is prescribed in accordance with the size of the diseased part 3a, and a patient collimator for edge enhancement, which further regulates the irradiation field of the diseased part 3a.

In this case, the pair of wobbler electromagnets 42a and 42b are arranged so that their magnetic fields may intersect orthogonally to each other within a plane orthogonal to the particle beam orbit. Besides, as shown in FIG. 3, the multi-leaf collimator 47 has leaves 47a set so as to agree with the shape of the diseased part 3a, whereby the planar irradiation field A of the particle beam is prescribed.

The irradiation control means 5 is configured of, for example, a controlling computer. It is configured of the accelerator system control portion 8 which controls the operations of the ion source 1, pre-stage accelerator 6, synchrotron accelerator 2a and beam transport system 7, an irradiation head control portion 9 which controls the irradiation head 4, and an irradiation system controller 10 which controls both the control portions 8 and 9 generally and collaboratively.

In addition, the irradiation head control portion 9 includes a wobbler power source control portion 92 which controls wobbler power sources 91a and 91b disposed individually for the respective wobbler electromagnets 42a and 42b, so as to subject these wobbler electromagnets 42a and 42b to magnetization and so as to deflect and scan the particle beam, and a range shifter control portion 93 which controls the range shifter 45 so that the irradiation energy of the particle beam may be altered in accordance with the size of the diseased part in the depth direction thereof. Besides, the monitor value of the irradiation dose as measured by the dose monitor 46 is accepted into the irradiation system controller 10.

Next, there will be described a control operation in the case where the particle beam is subjected to stacked conformation radiotherapy in the particle beam therapy apparatus having the above configuration.

Information items on particle beam characteristics required for the stacked conformation radiotherapy, such as the pulse width and pulse height of the particle beam, the number of pulses (irradiation dose) of each layer, the beam spill length Tb and the wobbler cycle Tw, are inputted to and set in the irradiation system controller 10 beforehand. The irradiation system controller 10 sends information items on the control of the accelerator system among the input information items, to the accelerator system control portion 8, and information items on the control of the irradiation head 4 to the irradiation head control portion 9, respectively.

Here, the particle beam generated by the ion source 1 is pre-accelerated by the pre-stage accelerator 6 and is further accelerated by the synchrotron accelerator 2a being the main accelerator, thereby to become the particle beam for therapeutical irradiation and to be emitted. This particle beam is guided to the irradiation head 4 via the beam transport system 7. In this case, the accelerator system control portion 8 controls the synchrotron accelerator 2a, whereby the energy intensity of the particle beam is basically set.

The particle beam guided to the irradiation head 4 is deflected into the direction of an irradiation point by the deflection electromagnet 41 of the irradiation head 4, and is thereafter deflected and scanned by the wobbler electromagnets 42a and 42b. Besides, the particle beam is scattered by the irradiation of the scatterer 43 so as to have the predetermined divergence angle, the energy width of the particle beam is subsequently extended by the ridge filter 44, and the kinetic energy intensity of the particle beam is thereafter shifted to a small value by the range shifter 45. Besides, the irradiation dose is monitored by the dose monitor 46, and the irradiation region of the particle beam is limited by the multi-leaf collimator 47 so as to irradiate the diseased part 3a in three dimensions.

On this occasion, the wobbler power source control portion 92 controls magnetization currents which are fed from the wobbler power sources 91a and 91b to the respective wobbler electromagnets 42a and 42b, so as to become the shapes of sinusoidal waves whose cycles are equal and whose phases are shifted 90 degrees from each other as shown in FIG. 4. Thus, the particle beam is deflected and scanned so as to depict a circular revolving orbit S within a plane perpendicular to its traveling direction. At that time, when a circle for one revolution is depicted by optimally setting a scattering angle ascribable to the scatterer 43 and the radius R of the revolving orbit S, two particle beam distributions P1 and P2 which pass through the center O of the circle of the revolving orbit S and which oppose to each other overlap, and a dose distribution P0 in a radial direction within the plane becomes flat, as shown in FIG. 5. Additionally FIG. 5 shows a principal for forming the flat dose distribution with wobbling motions by replacing two dimensional phenomenon with one dimensional phenomenon. However, in the case of considering a two-dimensional phenomenon, a two-dimensional dose distribution similarly becomes flat by the sum of beam spots of a circular orbit.

On the other hand, the accelerator system control portion 8 turns ON/OFF the gate of the synchrotron accelerator 2a for guiding the particle beam to the beam transport system 7, whereby the particle beam is emitted in time-division fashion with the pulse width (beam spill length) Tb which is longer than the wobbler cycle Tw expended in making one revolution of the circular orbit S, as shown in FIGS. 6A and 6B.

At that time, the accelerator system control portion 8 controls the timings of the emission start/stop so that the irradiation period (beam spill length) Tb of each pulse of the particle beam may become integral times the wobbler cycle Tw, as shown in FIG. 4, in other words, that Tb=n·Tw (where n denotes an integer) may hold. In the irradiation period Tb of each pulse of the particle beam, accordingly, the emission is always stopped at the point of time at which the particle beam has made n revolutions on the revolving orbit from an irradiation start point and returned to the irradiation start point again. That is, except for the irradiation period of the particle beam corresponding to one final pulse in each layer, the particle beam is always deflected and scanned so as to depict a complete round along the revolving orbit, irrespective of the timing of the emission stop of the particle beam, and the particle beam is not interrupted midway. Therefore, it is reliably avoidable that any irradiation lacking part appears on the revolving orbit S in the irradiation period Tb of each pulse of the particle beam. Actually, in the irradiation period of the particle beam corresponding to one final pulse in each layer, if particle beam current (which is relative to particle numbers per unit hour) is controlled in accordance with particle numbers irradiated in each layer, the particle beam is always deflected and scanned so as to depict an almost complete round along the revolving orbit so that the particle beam is not interrupted on the way. Consequently it is possible to obtain a more homogenized dose distribution.

Besides, the value of the irradiation dose as measured by the dose monitor 46 is accepted into the irradiation system controller 10. Therefore, when a predetermined number of pulses (irradiation dose) set for each layer beforehand has been reached, the accelerator system control portion 8 alters the number of pulses of the particle beam for the respective layers in succession and performs a control so that, as the irradiation region becomes shallower, the number of pulses per one layer may become smaller. Accordingly, as the irradiation region becomes shallower, the irradiation dose per one layer becomes lower.

Besides, the range shifter control portion 93 controls the range shifter 45, thereby to alter the irradiation energy of the particle beam every layer in correspondence with the depth L of the diseased part. Thus, extended Bragg peaks D1, D2, . . . are moved along the depth direction. In this manner, the irradiation dose is controlled every layer in the depth direction of the diseased part, and moreover, the extended Bragg peaks D1, D2, . . . are moved along the depth direction of the diseased part. As a result, the whole dose distribution Dt obtained by cumulating the extended Bragg peaks D1, D2, . . . of the respective layers is homogenized over the size L of the diseased part in the depth direction thereof as shown in FIG. 7.

In the stacked conformation radiotherapy, the number of wobbler revolutions per layer becomes smaller gradually as the hierarchy of the irradiation advances more (the irradiation region becomes shallower), as explained before. Since, however, the irradiation of the particle beam is not stopped midway of the revolving orbit at any layer or the number of the stop of the irradiation of the particle beam is only one, the frequency at which a place where parts lacking the particle beam irradiations overlap several layers appears as in the prior art becomes very low, and the stacked conformation radiotherapy which has the homogenized dose distribution at all times can be realized. Moreover, the timings of the magnetization currents of the wobbler electromagnets 42a and 42b and the timings of the emission/stop of the particle beam by the synchrotron accelerator 2a need not be brought into agreement, so that the particle beam irradiation control becomes simple.

Embodiment 2

FIG. 8 is a block diagram showing the principal portions of an irradiation head for projecting a particle beam toward an object to-be-irradiated and irradiation control means for performing the irradiation control of the particle beam, in a particle beam therapy apparatus in Embodiment 2 of the invention. Incidentally, identical numerals and signs shall be assigned to configurational portions which are correspondent or equivalent to those of Embodiment 1 shown in FIGS. 1 and 2.

In Embodiment 1 described before, the synchrotron accelerator 2a which emits the particle beam in the shape of pulses has been employed as the main accelerator. In contrast, here in Embodiment 2, stacked conformation radiotherapy is carried out by employing a cyclotron accelerator 2b which emits a particle beam continuously.

In this case, as shown in FIG. 9, the beam current intensity of an ion source 1 is altered by an accelerator system control portion 8, whereby the particle beam which has a predetermined particle beam intensity set every layer beforehand is drawn out from the cyclotron accelerator 2b.

Moreover, at that time, the accelerator system control portion 8 controls the ion source 1 and sets the irradiation period of the particle beam in each layer so as to become integral times a wobbler cycle. That is, letting "Tbi" denote the irradiation period of the particle beam in a certain ith layer, and "Tw" denote the wobbler cycle, the irradiation period is set so as to become:

$$Tbi = ni \cdot Tw \quad (1)$$

(where "ni" denotes an integer which is set in the ith layer)

Besides, in case of noticing the ith layer of a diseased part in the depth direction thereof, letting "Ni" denote the number of particles of the particle beam with which the pertinent layer is to be irradiated, "Tbi" denote the irradiation period of the particle beam for the pertinent layer, and "Ii" denote the beam current intensity in the ion source 1 as is necessary on this occasion, the following holds:

$$Ni = Tbi \cdot Ii / Q_0 \quad (2)$$

(where "$Q_0$" denotes the charge quantity of an electron)

From Formulas (1) and (2), the following is obtained:

$$Ii = Ni \cdot Q_0 / (ni \cdot Tw) \quad (3)$$

That is, when the beam current intensity Ii of the ion source 1 is previously set every layer on the basis of Formula (3), the irradiation period Tbi of the particle beam can be always set at the integral times ni of the wobbler cycle Tw while the number of particles Ni of the particle beam to irradiate each layer (in other words, an irradiation dose for each layer) is appropriately ensured. In that case, the number of particles Ni is determined every layer beforehand, the charge quantity $Q_0$ of the particle beam is determined by the sort of the particle beam, and the beam current of the ion source 1 is usually 30 nA or less. Therefore, the integer ni of each layer can be determined in conformity with Formula (3) so that the beam set current Ii may fall within a range of from several nA to 30 nA.

Next, there will be described a control operation in the case where the particle beam is subjected to the stacked conformation radiotherapy in the particle beam therapy apparatus having the above configuration.

Information items on particle beam characteristics required for the stacked conformation radiotherapy, such as that beam current intensity Ii of the ion source 1 in which the particle beam intensity of each layer is considered, the timings of the emission start/stop of the particle beam (the irradiation period Tbi) in each layer, and the wobbler cycle Tw, are inputted to and set in an irradiation system controller 10 so as to satisfy Formula (3) mentioned before. The irradiation system controller 10 sends information items on the control of an accelerator system among the input information items, to the accelerator system control portion 8, and information items on the control of an irradiation head 4 to the irradiation head control portion 9, respectively.

Since the accelerator system control portion 8 controls the beam current of the ion source 1 in accordance with each individual layer, the particle beam which has the particle beam intensity suitable for each layer is drawn out from the cyclotron accelerator 2b. In addition, the particle beam continuously emitted from the cyclotron accelerator 2b is guided to the irradiation head 4. On this occasion, wobbler power sources 91a and 91b magnetize respective wobbler electromagnets 42a and 42b under the control of a wobbler power source control portion 92, so that the particle beam is deflected and scanned so as to depict a circular revolving orbit within a plane perpendicular to its traveling direction.

In this case, the beam current intensity Ii of the ion source 1 is previously set for each layer as indicated by Formula (3) mentioned before, and hence, the irradiation period Tbi of the certain ith layer corresponds just to the integral times ni of the wobbler cycle Tw of the wobbler electromagnets 42a and 42b. In the particle beam irradiation of the certain ith layer, accordingly, an irradiation dose which is monitored by a dose monitor 46 arrives at a preset value at the point of time at which the particle beam has made ni revolutions on the revolving orbit from an irradiation start point and returned to the irradiation start point. Then, the irradiation system controller 10 reports to that effect to the accelerator system control portion 8, so that the accelerator system control portion 8 stops the particle beam irradiation of the ith layer. Therefore, even in the case where the continuous beam is emitted from the cyclotron accelerator 2b, a more homogeneous dose distribution can be formed in an irradiation field.

Besides, in the same manner as in the case of Embodiment 1, the range shifter control portion 93 controls the range shifter 45, thereby to alter the irradiation energy of the particle beam every layer in correspondence with the depth L of the diseased part. Therefore, extended Bragg peaks D1, D2, . . . are moved along the depth direction. In this manner, the irradiation dose is controlled every layer in the depth direction of the diseased part, and moreover, the extended Bragg peaks D1, D2, . . . are moved along the depth direction of the diseased part. As a result, the whole dose distribution Dt obtained by cumulating the extended Bragg peaks D1, D2, . . . of the respective layers is homogenized over the depth L of the diseased part as shown in FIG. 11.

As thus far described, also in Embodiment 2, the irradiation period Tb of each layer is set at the integral times of the wobbler cycle Tw. Therefore, the particle beam is always deflected and scanned so as to depict a complete round along the revolving orbit S, irrespective of the timing of the emission stop of the particle beam, and the particle beam is not interrupted midway. Accordingly, it is reliably avoidable that any irradiation lacking part appears on the last revolving orbit S of each layer, and the stacked conformation radiotherapy which has the homogenized dose distribution at all times can be realized. Moreover, the timings of the magnetization currents of the wobbler electromagnets 42a and 42b and the timings of the emission/stop of the particle beam of the ion source 1 need not be brought into agreement, so that the particle beam irradiation control becomes simple.

Incidentally, here in Embodiment 2, the cutoff of the particle beam at the fulfillment of the irradiation dose of each layer is performed by controlling the ion source 1. However, the particle beam cutoff can also be performed by disposing a kicker electromagnet or the like midway of the beam transport system 7 which extends from the cyclotron accelerator 2b to the irradiation head 4.

Besides, in the above description, the quantity ni in Formula (3) has been stated as being set just at the integer, but the quantity ni need not be strictly integral in actuality. The reason therefor is as explained below. The particle beam which is deflected and scanned by the wobbler electromagnets 42a and 42b is endowed with a sufficiently large spot size by the scatterer 43 or the like. Therefore, even when the particle beam does not depict the strict complete round, particle beam distributions overlap, and hence, the dose distribution in a radial direction becomes flat within the plane. Accordingly, the quantity ni may be a value approximate to the integer, and the same advantages as stated above can be attained.

Since the remaining configuration and functional effects are the same as in the case of Embodiment 1, they shall be omitted from detailed description here.

Embodiment 3

FIG. 12 is a block diagram showing the principal portions of an irradiation head for projecting a particle beam toward an object to-be-irradiated and irradiation control means for performing the irradiation control of the particle beam, in a particle beam therapy apparatus in Embodiment 3 of the invention. Incidentally, identical numerals and signs shall be assigned to configurational portions which are correspondent or equivalent to those of Embodiment 1 shown in FIGS. 1 and 2.

The synchrotron accelerator 2a from which the particle beam is emitted with the pulse width (beam spill length) Tb longer than the wobbler cycle Tw has been used in Embodiment 1 described before, and the cyclotron accelerator 2b from which the particle beam is continuously emitted has been used in Embodiment 2. In contrast, here in Embodiment 3, a linear accelerator 2c from which the particle beam is emitted with a pulse width Tq shorter than the wobbler cycle Tw is employed. Incidentally, the synchrotron accelerator can be applied apart from the linear accelerator 2c.

In this case, the number of pulses of the particle beam which is emitted from the linear accelerator 2c is altered every layer by an accelerator system control portion 8 so that an appropriate irradiation dose may be given every layer. Moreover, at that time, as to an irradiation period Tri in each layer, the integral times of the emission cycle Tp of the particle beam pulses are set so as to become the integral times of the wobbler cycle Tw, as shown in FIG. 13. That is, the following is set:

$$Tri = ki \cdot Tp = ni \cdot Tw \quad (4)$$

(where "ki" and "ni" denote integers which are respectively set in the ith layer)

Next, there will be described a control operation in the case where the particle beam is subjected to the stacked conformation radiotherapy in the particle beam therapy apparatus having the above configuration.

Information items on particle beam characteristics required for the stacked conformation radiotherapy, such as the irradiation period Tri of each layer, the number of pulses ki of the particle beam pulses, the emission cycle Tp of the particle beam pulses, the pulse width Tq, a pulse height and the wobbler cycle Tw, are inputted to and set in an irradiation system controller 10 so as to satisfy Formula (4) mentioned before. The irradiation system controller 10 sends information items on the control of an accelerator system among the input information items, to the accelerator system control portion 8, and information items on the control of the irradiation head 4 to the irradiation head control portion 9, respectively.

Since the accelerator system control portion 8 controls the ion source 1 and the linear accelerator 2c in accordance with each individual layer, the particle beam pulses which have the pulse width Tq being a period shorter than the wobbler cycle Tw are emitted from the linear accelerator 2c with the predetermined cycle Tp. In addition, the particle beam pulses emitted from the linear accelerator 2c are guided to the irradiation head 4. On this occasion, wobbler power sources 91a and 91b magnetize respective wobbler electromagnets 42a and 42b under the control of the wobbler power source control portion 92, so that the particle beam pulses are deflected and scanned so as to depict a circular revolving orbit S within a plane perpendicular to their traveling direction.

In this case, the pulse width Tq of each of the particle beam pulses emitted from the linear accelerator 2c is shorter than the wobbler cycle Tw, and hence, the central points of the irradiation regions P of the respective pulses are discretely existent along the revolving orbit S. However, the particle beam is scattered by the scatterer 43 or the like, and it has a sufficiently large spot size as shown in FIG. 14. Therefore, when a circle for one revolution is depicted, two particle beam distributions which pass through the center O of the circle of the revolving orbit S and which oppose to each other overlap, and a dose distribution in a radial direction within the plane becomes flat.

Besides, as indicated in Formula (4) mentioned before, the integral times of the emission cycle Tp of the particle beam pulses in each layer are set so as to become the integral times of the wobbler cycle Tw, so that the irradiation period Tri of, for example, the ith layer corresponds to the integral times ni of the wobbler cycle Tw. In the particle beam irradiation of the ith layer, therefore, the particle beam pulses have been projected ki times at the point of time at which the particle beam has made ni revolutions on the revolving orbit from an irradiation start point and returned to the irradiation start point to stop the irradiation (that is, at the point of time at which the period Tri has lapsed). Accordingly, even in the case where the particle beam pulses having the pulse width Tq shorter than the wobbler cycle Tw are emitted from the linear accelerator 2c, a homogeneous dose distribution can be formed in an irradiation field.

Besides, in the same manner as in the case of Embodiment 1, a range shifter control portion 93 controls the range shifter 45, thereby to alter the irradiation energy of the particle beam every layer in correspondence with the depth L of the diseased part. Therefore, extended Bragg peaks are moved along the depth direction. As a result, the dose distribution Dt obtained by cumulating the extended Bragg peaks of the respective layers is homogenized over the depth L of the diseased part as shown in FIG. 7 or FIG. 11.

As thus far described, in Embodiment 3, even when the accelerator 2c which emits the particle beam of the pulse width Tq shorter than the wobbler cycle Tw is employed, it is reliably avoidable that any irradiation lacking part appears on the last revolving orbit of each layer, and the stacked conformation radiotherapy which has the homogenized dose distribution at all times can be realized. Moreover, the timings of the magnetization currents of the wobbler electromagnets 42a and 42b and the timings of the emission/stop of the particle beam of the ion source 1 need not be brought into agreement, so that the particle beam irradiation control becomes simple.

Since the remaining configuration and functional effects are the same as in the case of Embodiment 1, they shall be omitted from detailed description here.

Incidentally, Embodiments 1-3 have been described as to the case of homogenizing the dose distribution in such a way that the particle beam is deflected and scanned so as to depict the circular orbit on the plane, by the magnetizations of the wobbler electromagnets 42a and 42b. However, this aspect is not restrictive, but the dose distribution on the plane can be homogenized even in a case where, as shown in FIG. 15 by way of example, the particle beam is deflected and scanned so as to depict a zigzag revolving orbit which begins with a start point and returns to the start point.

Various modifications and alterations of the present invention will be apparent to those skilled in the art without departing from the scope and spirit of the invention, and it should be understood that the invention is not limited to the illustrative embodiments set forth herein.

What is claimed is:

1. A stacked conformation radiotherapy system comprising an accelerator which accelerates a particle beam generated from an ion source, an irradiation head which projects the particle beam accelerated by said accelerator, toward an object to-be-irradiated, and which includes wobbler electromagnets for deflecting and scanning the particle beam, and an irradiation controller for carrying out stacked conformation radiotherapy by controlling the ion source, said accelerator and said irradiation head, said irradiation controller deflecting and scanning the particle beam by subjecting the wobbler electromagnets to magnetization controls;

wherein said irradiation controller performs the magnetization controls of the wobbler electromagnets so that the particle beam depicts a one-stroke revolving orbit which begins with a start point and returns to the start point, controls an irradiation dose of the stacked conformation radiotherapy in a depth direction of the object to be irradiated by altering a particle beam intensity layer by layer, and sets a total emission period of the particle beam to be outputted from said accelerator, prior to irradiation, such that the total emission period in each layer is an integral multiple of a wobbler cycle which is required for the particle beam to make one revolution of the revolving orbit.

2. A stacked conformation radiotherapy system as defined in claim 1, wherein said accelerator is an accelerator which emits the particle beam with a pulse width longer than the wobbler cycle, and wherein said irradiation controller alters the number of the particle beams every layer of the stacked conformation radiotherapy, thereby to control an irradiation dose of each layer in a depth direction of the object to-be-irradiated, and it performs a control so that the emission period of each pulse of the particle beam is an integral multiple of the wobbler cycle.

3. A stacked conformation radiotherapy system as defined in claim 1, wherein said accelerator is an accelerator which emits the particle beam with a pulse width shorter than the wobbler cycle, and wherein said irradiation controller alters the number of pulses of the particle beam every layer of the stacked conformation radiotherapy, thereby controlling the irradiation dose of each layer and performs a control so that an integral multiple of an emission cycle of the pulses of the particle beam is an integral multiple of the wobbler cycle.

4. A stacked conformation radiotherapy system as defined in claim 1, wherein in addition to the control of the irradiation dose of each layer in the depth direction of the object to-be-irradiated, said irradiation controller alters irradiation energy of the particle beam every layer, thereby to perform a control so that the dose distribution in the depth direction of the object to-be-irradiated is flat.

5. A stacked conformation radiotherapy system as defined in claim 1, wherein the one-stroke revolving orbit is a circular orbit or a zigzag orbit.

6. A particle beam therapy apparatus comprising the stacked conformation radiotherapy system as defined in claim 1.

* * * * *